United States Patent
Bae et al.

(10) Patent No.: US 10,188,351 B2
(45) Date of Patent: Jan. 29, 2019

(54) ELECTROCARDIOGRAM (ECG) SIGNAL BASED AUTHENTICATION APPARATUS AND METHOD

(71) Applicants: SAMSUNG ELECTRONICS CO., LTD., Suwon-si (KR); Korea Advanced Institute of Science and Technology, Daejeon (KR)

(72) Inventors: Chisung Bae, Yongin-si (KR); Jin Woo Shin, Daejeon (KR); Sung-Soo Ahn, Daejeon (KR); Sang Joon Kim, Hwaseong-si (KR)

(73) Assignees: Samsung Electronics Co., Ltd., Suwon-si (KR); Korea Advanced Institute of Science and Technology, Daejeon (KR)

( * ) Notice: Subject to any disclaimer, the term of this patent is extended or adjusted under 35 U.S.C. 154(b) by 0 days.

(21) Appl. No.: 15/246,712

(22) Filed: Aug. 25, 2016

(65) Prior Publication Data

US 2017/0215806 A1 Aug. 3, 2017

(30) Foreign Application Priority Data

Feb. 1, 2016 (KR) .......................... 10-2016-0012179

(51) Int. Cl.
*A61B 5/117* (2016.01)
*A61B 5/00* (2006.01)
*A61B 5/0452* (2006.01)
*G06F 21/32* (2013.01)
*G06K 9/00* (2006.01)

(52) U.S. Cl.
CPC .......... *A61B 5/7264* (2013.01); *A61B 5/0452* (2013.01); *A61B 5/117* (2013.01); *G06F 21/32* (2013.01); *A61B 5/6898* (2013.01); *G06K 2009/00939* (2013.01)

(58) Field of Classification Search
CPC ... A61B 5/04525; A61B 5/117; A61B 5/1171; A61B 5/7246; A61B 5/7264; A61B 5/7267
See application file for complete search history.

(56) References Cited

U.S. PATENT DOCUMENTS

| 7,630,521 | B2 * | 12/2009 | Kim ................... G06K 9/00496 382/115 |
| 7,689,833 | B2 | 3/2010 | Lange |
| 8,121,972 | B2 | 2/2012 | Snyder |
| 8,750,973 | B2 | 6/2014 | Katz et al. |
| 9,144,389 | B2 | 9/2015 | Srinivasan et al. |
| 9,547,820 | B2 * | 1/2017 | Kim ........................ G06N 3/08 |

(Continued)

FOREIGN PATENT DOCUMENTS

| EP | 2712454 A1 | 4/2014 |
| JP | 5-207985 A | 8/1993 |

(Continued)

*Primary Examiner* — Eugene T Wu
(74) *Attorney, Agent, or Firm* — NSIP Law

(57) ABSTRACT

An authentication apparatus includes one or more processors configured to temporally implement a neural network, used to extract a feature value from hidden nodes, that is connected to input nodes to which an electrocardiogram (ECG) signal is input so as to share a weight set with the input nodes, and to match the ECG signal and the extracted feature value to a user for registration.

8 Claims, 12 Drawing Sheets

(56) References Cited

U.S. PATENT DOCUMENTS

| | | | |
|---|---|---|---|
| 2006/0215883 A1* | 9/2006 | Kim | G06K 9/00496 |
| | | | 382/115 |
| 2013/0117207 A1* | 5/2013 | Kim | G06N 3/08 |
| | | | 706/20 |
| 2014/0361871 A1 | 12/2014 | Silva et al. | |
| 2015/0125049 A1* | 5/2015 | Taigman | G06K 9/00268 |
| | | | 382/118 |
| 2015/0206364 A1 | 7/2015 | Agrafioti et al. | |
| 2017/0188971 A1* | 7/2017 | Liu | A61B 5/0006 |

FOREIGN PATENT DOCUMENTS

| | | |
|---|---|---|
| KR | 10-0718125 B1 | 5/2007 |
| KR | 10-0750662 B1 | 8/2007 |
| KR | 10-0887766 B1 | 3/2009 |
| KR | 10-1270954 B1 | 6/2013 |
| KR | 10-2013-0140439 A | 12/2013 |
| KR | 10-2014-0097039 A | 8/2014 |
| WO | WO 2012/151680 A1 | 11/2012 |

\* cited by examiner

260

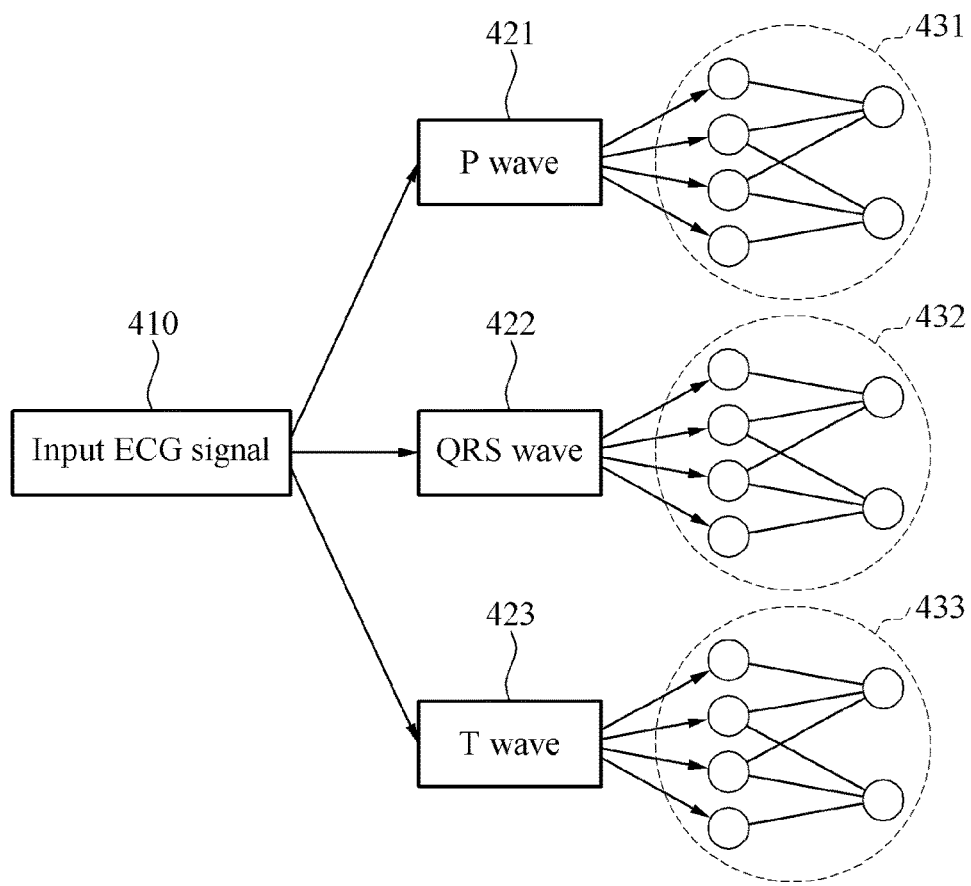

500

ELECTROCARDIOGRAM (ECG) SIGNAL BASED AUTHENTICATION APPARATUS AND METHOD

CROSS-REFERENCE TO RELATED APPLICATIONS

This application claims the benefit under 35 USC 119(a) of Korean Patent Application No. 10-2016-0012179 filed on Feb. 1, 2016 in the Korean Intellectual Property Office, the entire disclosure of which is incorporated herein by reference for all purposes.

BACKGROUND

1. Field

The following description relates to electrocardiogram (ECG) signal based authentication technology. For example, the following description relates to an electrocardiogram (ECG) signal based authentication apparatus. The following description also relates to an electrocardiogram (ECG) signal based authentication method.

2. Description of Related Art

Wearable devices implemented in wearable forms, for example, glasses, a watch, and clothing have been commercialized. For example, users may contact the wearable devices to acquire desired information from the wearable devices. The wearable devices may acquire biosignals such as electroencephalogram (EEG) signals and electromyogram (EMG) signals of the user. In general, a wearable device may include an authentication system for verifying whether a user in contact with the wearable device is a registered user. The wearable device may identify the user by receiving a fingerprint, a voice, or user information input through a touch interface, thereby authenticating the user.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an authentication apparatus includes one or more processors configured to temporally implement a neural network, used to extract a feature value from hidden nodes, that is connected to input nodes to which an electrocardiogram (ECG) signal is input so as to share a weight set with the input nodes, and match the ECG signal and the extracted feature value to a user for registration.

The authentication apparatus may further include a memory, wherein the processor uses the memory to match the ECG signal and the extracted feature value to the user for registration.

The neural network may include the hidden nodes connected with input node sets, each of the input node sets including a number of input nodes connected through a machine learning.

The neural network may be configured to sequentially connect the hidden nodes to the input node sets.

The one or more processors may further include a signal separator configured to separate at least one interval signal of a P wave, a QRS wave, and a T wave from the ECG signal, and the neural network may be configured to apply the weight set determined based on the at least one interval signal to calculate an output value.

The neural network may include at least one of a first sub-neural network having a first weight set corresponding to the P wave, a second sub-neural network having a second weight set corresponding to the QRS wave, or a third sub-neural network having a third weight set corresponding to the T wave.

A number of nodes included in each of the three sub-neural networks and weights to be assigned to the nodes may be determined based on a result of machine learning.

The machine learning may be performed using a Siamese neural network.

The neural network may be configured to select an upper value in a range from feature values corresponding to the hidden nodes.

In another general aspect, an authentication apparatus includes a calculator configured to calculate a first output value corresponding to an input electrocardiogram (ECG) signal and second output values corresponding to a reference ECG signal based on a neural network at least temporally implemented by one or more processors, an extractor configured to extract a number of second output values from the second output values based on the first output value, and a determiner configured to determine whether to authenticate a user associated with the input ECG signal based on a ratio of a number of the extracted second output values that are associated with a registered user to a total number of the extracted second output values.

The reference ECG signal may include an ECG signal associated with an unidentified user and an ECG signal associated with the registered user, and the calculator may be further configured to calculate second output values corresponding to the unidentified user and the registered user.

The extractor may be configured to extract the number of second output values in a descending order of similarities with the first output value.

The extractor may be configured to repetitively extract second output values from the second output values, a number of the extracted second output values being different for each extraction, and the determiner may be configured to determine whether to authenticate the user based on the ratio through a repetitive calculation.

The determiner may be further configured to authenticate the user associated with the input ECG signal to be the registered user in response to the ratio of the number of the extracted second output values associated with the registered user to the total number of the extracted second output values having a highest value.

The determiner may be further configured to authenticate the user associated with the input ECG signal to be the registered user in response to the ratio of the number of the extracted second output values associated with the registered user to the total number of the extracted second output values being higher than or equal to a threshold.

The authentication apparatus may further include a memory configured to store the reference ECG signal, wherein, in response to the user being authenticated as the registered user, the determiner is configured to store the input ECG signal in the memory as a part of the reference ECG signal in association with the registered user.

The memory may be configured to store ECG signals corresponding to different points in time as the reference ECG signal.

In another general aspect, a wearable device includes a sensor configured to acquire an input electrocardiogram (ECG) signal from a body of a user in contact with the wearable device, a processor configured to calculate a first output value corresponding to the input ECG signal and second output values corresponding to a reference ECG signal based on a neural network, extract a number of second output values from the second output values based on the first output value, and authenticate the user based on a ratio of a number of the extracted second output values that are associated with a registered user to a total number of the extracted second output values, and a display configured to output an authentication result to the user.

The processor may be further configured to extract the number of second output values from the second output values in a descending order of similarities with the first output value.

The processor may be configured to determine the user to be the registered user in response to the ratio of the extracted second output values associated with the registered user being higher than or equal to a threshold.

Other features and aspects will be apparent from the following detailed description, the drawings, and the claims.

BRIEF DESCRIPTION OF THE DRAWINGS

FIGS. 4A and 4B are diagrams illustrating an example of generating a sub-neural network for each interval signal of an ECG signal in accordance with an embodiment.

Throughout the drawings and the detailed description, the same reference numerals refer to the same elements. The drawings may not be to scale, and the relative size, proportions, and depiction of elements in the drawings may be exaggerated for clarity, illustration, and convenience.

DETAILED DESCRIPTION

Figure 1:
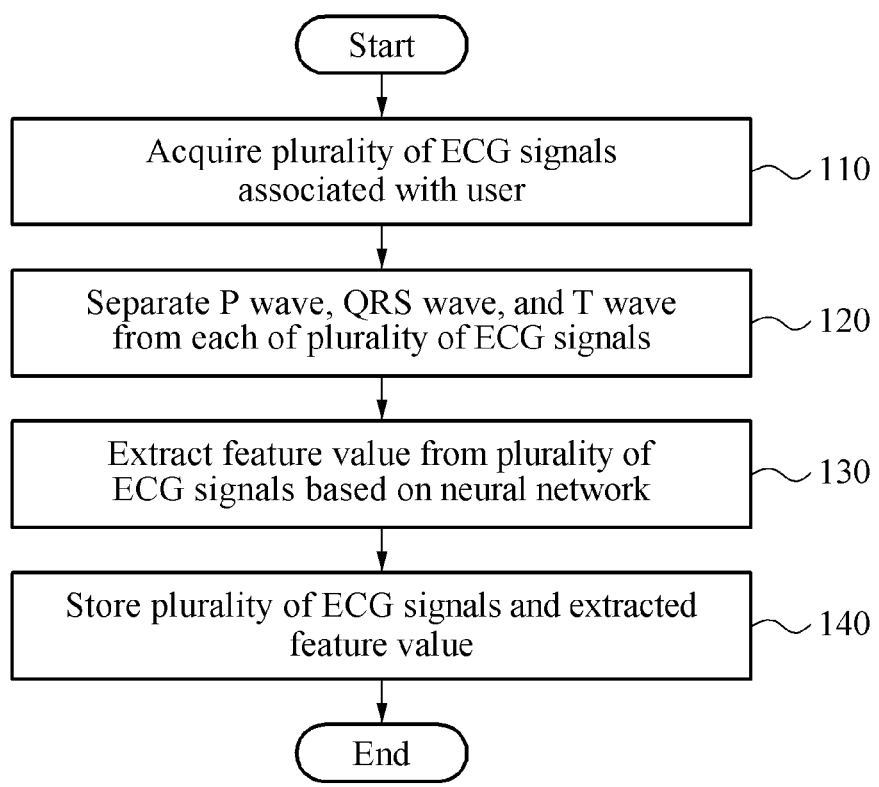
FIG. 1 is a flowchart illustrating an example of an authentication apparatus for registering an electrocardiogram (ECG) signal in accordance with an embodiment.

The following detailed description is provided to assist the reader in gaining a comprehensive understanding of the methods, apparatuses, and/or systems described herein. However, various changes, modifications, and equivalents of the methods, apparatuses, and/or systems described herein will be apparent to one of ordinary skill in the art. The sequences of operations described herein are merely examples, and are not limited to those set forth herein, but may be changed as will be apparent to one of ordinary skill in the art, with the exception of operations necessarily occurring in a certain order. Also, descriptions of functions and constructions that are well known to one of ordinary skill in the art may be omitted for increased clarity and conciseness.

The features described herein may be embodied in different forms, and are not to be construed as being limited to the examples described herein. Rather, the examples described herein have been provided so that this disclosure will be thorough and complete, and will convey the full scope of the disclosure to one of ordinary skill in the art.

Terms such as first, second, A, B, (a), (b), and the like may be used herein to describe components. However, each of these terms is not used to define an essence, order or sequence of a corresponding component but is used merely to distinguish the corresponding component from other component(s). For example, a first component may be referred to a second component, and similarly the second component may also be referred to as the first component, but these terms are used to indicate that the first component and the second component are separate components.

It is to be noted that if it is described in the specification that one component is "connected," "coupled," or "joined" to another component, a third component may be "connected," "coupled," and "joined" between the first and second components, although the first component may be directly connected, coupled or joined to the second component. In addition, it is to be noted that if it is described in the specification that one component is "directly connected" or "directly joined" to another component, a third component may not be present therebetween. Likewise, expressions, for example, "between" and "immediately between" and "adjacent to" and "immediately adjacent to" may also be construed as described in the foregoing with respect to their meaning with respect to the relationship between the terms they are used to pertain to.

The terminology used herein is for the purpose of describing particular examples only, and is not to be used to limit the disclosure. As used herein, the terms "a," "an," and "the" are intended to include the plural forms as well, unless the context clearly indicates otherwise. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof.

Unless otherwise defined, all terms, including technical and scientific terms, used herein have the same meaning as commonly understood by one of ordinary skill in the art to which this disclosure pertains. Terms, such as those defined in commonly used dictionaries, are to be interpreted as having a meaning that is consistent with their meaning in the context of the relevant art, and are not to be interpreted in an idealized or overly formal sense unless expressly so defined herein.

The following examples are applied to recognize an electrocardiogram (ECG) signal of a user. Subsequently, an operation of recognizing the ECG signal of the user includes an operation of recognizing the ECG signal to verify or identify the user. For example, an operation of authentication of the user includes an operation of determining whether the user is a pre-registered user. In this example, a result of the operation of authentication the user is to be output as true or false. The authentication produces a true result when the identity of the user matches the pre-registered identity and produces a false result when the identity of the user does not match the pre-registered user.

An operation of identifying the user includes an operation of determining a user corresponding to the user from among a plurality of registered users. In this example, a result of the operation of identifying the user is to be output as an identification (ID) of one of the plurality of registered users. For example, the identification may be a numeric ID or an alphanumeric ID. When the user does not correspond to any one of the plurality of the registered users, a signal indicating that the user is not identified may be output. The following examples are implemented through, for example, using a wearable device including a sensor configured to acquire an ECG signal of a body of a user and a display configured to output an authentication result of the user based on the acquired signal.

Hereinafter, example embodiments are described in further detail with reference to the accompanying drawings. Regarding the reference numerals assigned to the elements in the drawings, it is to be noted that the same elements are designated by the same reference numerals and repeated descriptions are omitted.

FIG. 1 is a diagram illustrating an example of an authentication apparatus for registering an ECG signal in accordance with an embodiment.

In an example, a neural network indicates a computing device configured to perform a machine learning based on input data. The input data corresponds to a biosignal of a user acquired through using a sensing device. For example, the sensing device is implemented as a wearable device. In such an example, the biosignal is an ECG signal. The neural network is at least temporally implemented by at least one processor included in an authentication apparatus, such that the neural network changes over time based on the operation provided by the at least one processor. In the following examples, nodes are understood to be artificial neurons included in the neural network.

Referring to FIG. 1, a method 100 of registering an ECG signal is performed by an authentication apparatus. Thus, in an example, the following method steps are performed by such an authentication apparatus. In operation 110, the method acquires a plurality of ECG signals associated with a user. An ECG signal represents, for example, an ECG period including a P wave, a QRS wave, and a T wave. In such an example, the P wave represents atrial depolarization, the QRS wave or QRS complex represents ventricular depolarization, and the T wave represents ventricular repolarization. Thus, in operation 110, the method acquires the plurality of ECG signals corresponding to a plurality of ECG periods.

In operation 120, the method separates the P wave, the QRS wave, and the T wave from each signal of the plurality of ECG signals. As an example, when the method acquires 100 ECG signals of the user in operation 110, the method extracts 100 P waves, 100 QRS waves, and 100 T waves from the 100 ECG signals in operation 120.

In operation 130, the method extracts a feature value from the plurality of ECG signals based on the neural network. The feature value indicates, for example, a result value of the machine learning performed based on the neural network. In an example, a similar feature value is obtained with respect to the same ECG signals and different feature values are obtained with respect to different ECG signals. The authentication apparatus extracts a feature value from an ECG signal of a registered user and determine whether a predetermined ECG signal is a registered ECG signal associated with the registered user by comparing the predetermined ECG signal and the extracted ECG signal. A process of the determining is described in further detail later with reference to the drawing below.

In operation 140, the method stores the plurality of ECG signals and the extracted feature values. As an example, the method stores a plurality of feature values corresponding to the plurality of ECG signals. As another example, the method acquires a representative ECG signal by performing normalization on the plurality of ECG signals and stores a feature value corresponding to the representative ECG signal. As still another example, the method calculates the plurality of feature values corresponding to the plurality of ECG signals and stores an average value of the plurality of feature values as the representative feature value. The aforementioned operations of storing the ECG signals and the feature value in the authentication apparatus for a user authentication are described as an example only. Thus, the present examples are not to be taken as being limited thereto.

A process in which the authentication apparatus extracts a feature value using an input layer node and a hidden layer node included in a neural network will be described in detail later with reference to the drawing below.

Figure 2A:
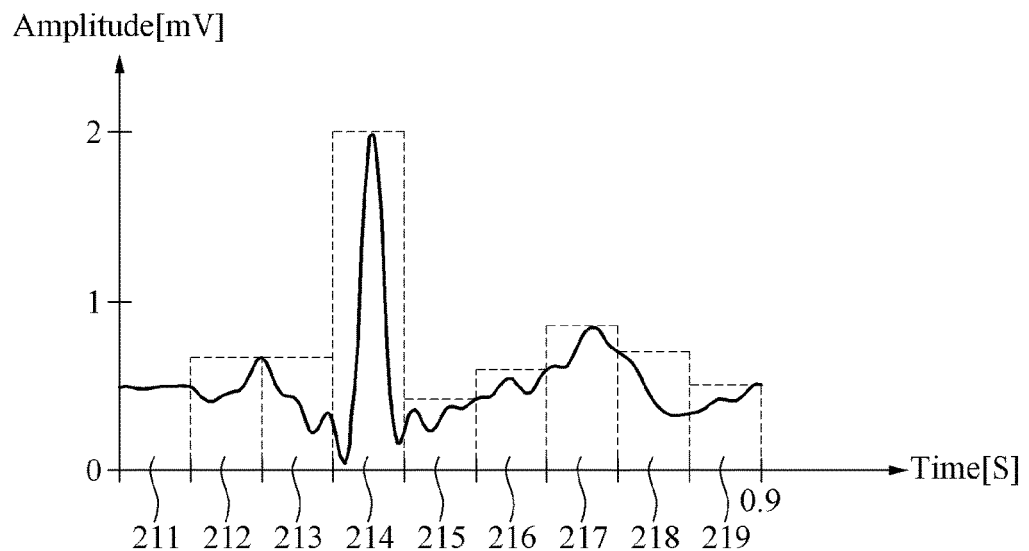
FIGS. 2A and 2B are diagrams illustrating an example of extracting a feature value from an input ECG signal in accordance with an embodiment.
Figure 2B:
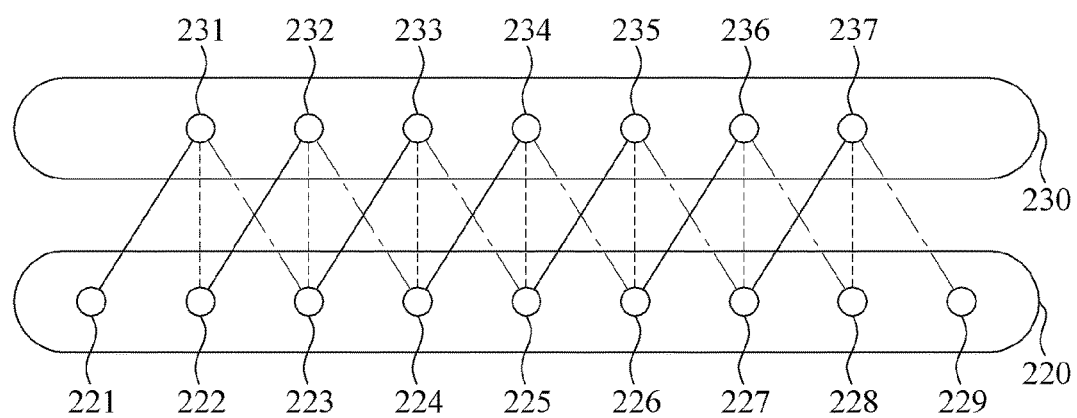

FIGS. 2A and 2B are diagrams illustrating an example of extracting a feature value from an input ECG signal in accordance with an embodiment.

FIG. 2A illustrates a graph of an ECG signal input to an authentication apparatus. In the graph, an X axis represents a time in seconds and a Y axis represents an amplitude of the input ECG signal based on a unit of millivolts (mV). For example, the input ECG signal is a signal obtained by preprocessing a biosignal of a user. Various sources and characteristics of such a biosignal have been discussed further, above. The authentication apparatus filters the biosignal to remove a noise signal and detects a peak. In an example, the authentication apparatus detects an R peak of a QRS wave of the ECG signal. Also, the authentication apparatus generates a template of the ECG signal based on the peak, performs normalization, and detects an outlier. As the preprocessing of the authentication apparatus performed on the input ECG signal may be performed using existing techniques, descriptions of such are omitted for brevity.

The authentication apparatus generates ECG signals, for example, a first sampled ECG signal 211 to a ninth sampled ECG signal 219. The ECG signals are sampled to correspond to preset time intervals based on the input ECG signal. FIG. 2A illustrates nine sampled ECG signals as an example. Thus, the number of sampled ECG signals is not construed as being limited to the example described herein. Accordingly, the authentication apparatus also operates based having the number of sampled ECG signals varying according to another appropriate example.

FIG. 2B illustrates an input layer node 220 and a hidden layer node 230 included in the authentication apparatus. The input layer node 220 includes at least one input node, for example, a first input node 221 to a ninth input node 229. The first sampled ECG signals to the ninth sampled ECG signal 219 are input to the first input node 221 to the ninth input node 229, respectively. For example, the first sampled ECG signal 211 is input to the first input node 221. The hidden layer node 230 includes at least one hidden node, for example, a first hidden node 231 to a seventh hidden node 237.

The authentication apparatus groups a preset number of input nodes, for example, the first input node 221, a second input node 222, and a third input node 223 into a first input node set. Similarly, the authentication apparatus groups the second input node 222, the third input node 223, and a fourth input node 224 into a second input node set. Also, the authentication apparatus groups a seventh input node 227, an eighth input node 228, and the ninth input node 229 into a third input node set. FIG. 2B illustrates that three input nodes are grouped into one input node set as an example. However, the present disclosure is not limited to the aforementioned example and thus, various alternative groupings of input nodes are applicable in other examples.

The authentication apparatus calculates an output value corresponding to the input ECG signal based on the neural network. That is, the input ECG is fed into the neural network, which has learned ways to consider such inputs to associate the inputs with user identifications. The output value indicates, for example, a feature value used to identify or authenticate a user. The authentication apparatus assigns an identical weight set to the first input node set and calculates an output value corresponding to a first hidden node, for example, the hidden node 231. Similarly, the authentication apparatus assigns the identical weight set to the second input node set and the third input node set and calculates output values corresponding to a second hidden node, for example, the hidden node 232 and a third hidden node, for example, the hidden node 233.

To calculate the output value corresponding to the first hidden node 231, a weight set including weights of 0.3, 0.5, and 0.2 is applied to the first sampled ECG signal 211, the second sampled ECG signal 212, and the third sampled ECG signal 213 corresponding to the first input node set. For example, 0.3 is applied to the first sampled ECG signal 211, 0.5 is applied to the second sampled ECG signal 212, and 0.2 is applied to the third sampled ECG signal 213. Similarly, to calculate the output value corresponding to the second hidden node 232, the same weight set including 0.3, 0.5, and 0.2 is applied to the second sampled ECG signal 212, the third sampled ECG signal 213, and the fourth sampled ECG signal 214 corresponding to the second input node set. Through this, 0.3 is applied to the second sampled ECG signal 212, 0.5 is applied to the third sampled ECG signal 213, and 0.2 is applied to the fourth sampled ECG signal 214. In such an example, the first hidden node 231 through the seventh hidden node 237 are connected to the first input node 221 through the ninth input node 229 based on a weight set shared between the nodes, as discussed above, which allows machine learning to take place in a way that facilitates recognition by using the applied weights such that the sampled ECG signals are successfully usable to generate recognition results.

The ECG signal varies based on a state of a user's heart, such as a physiological state of the user's heart. For example, an ECG assesses the electrical and muscular functions of the heart. A position of a peak in an ECG signal corresponding to one period may vary based on the state of user, for example, an excited state, a lack of sleep, and an excessive consumption of caffeine. In an example, the authentication apparatus groups input nodes in a neural network into input node sets and applies an identical weight set to the input node sets. For example, nodes from among a plurality of hidden nodes included in the neural network share the identical weight set to be connected with the input nodes. When an ECG signal input to a plurality of input nodes corresponds to a preset time interval, the authentication apparatus outputs an identical output value or an output value in a preset error range as a feature value. Thus, the authentication apparatus that uses such an approach more stably performs a user authentication irrespective of noise or a change in the state of user, in that it is able to use the neural network to learn which certain feature patterns are to be associated with which authentication outcomes.

Figure 2C:
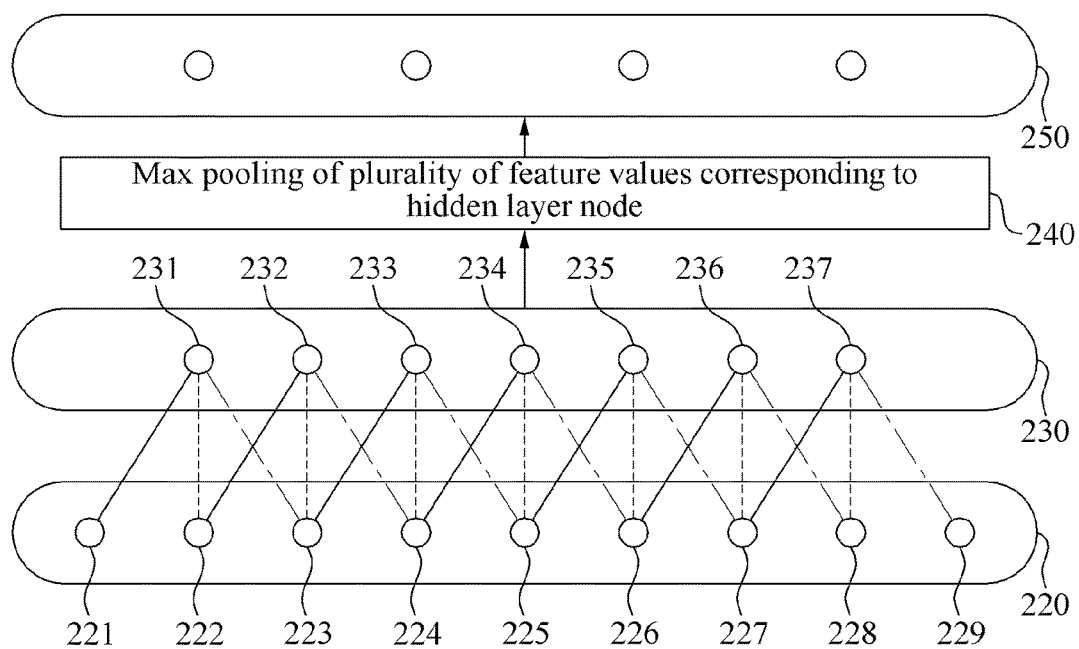
FIG. 2C is a diagram illustrating an example of a sub-neural network in accordance with an embodiment.

FIG. 2C is a diagram illustrating an example of a sub-neural network in accordance with an embodiment.

FIG. 2C illustrates a sub-neural network for extracting a feature value. The sub-neural network includes the input layer node 220 including a plurality of input nodes, for example, the first input node 221 to the ninth input node 229, and the hidden layer node 230 including a plurality of hidden nodes, for example, the first hidden node 231 to the seventh hidden node 237. As discussed in the foregoing explanation, an identical weight set is shared in the hidden layer node 230 and the hidden layer node 230 is connected to the input layer node 220. Because the descriptions of FIGS. 2A and 2B are applicable here, repeated descriptions related to FIG. 2C are omitted for brevity.

In FIG. 2C, the sub-neural network corresponds to at least one interval signal of a P wave, a QRS wave, and a T wave included in an ECG signal. These various waveforms are discussed further, above. In such an example, an authentication apparatus includes at least one sub-neural network. For example, the authentication apparatus includes at least one of a first sub-neural network having a first weight set corresponding to the P wave, a second sub-neural network having a second weight set corresponding to the QRS wave, and a third sub-neural network having a third weight set corresponding to the T wave. By including information related to these weight sets, an embodiment is able to achieve improved analysis results of the ECG signal.

For example, the ECG signal is separated into the P wave, the QRS wave, and the T wave based on a movement of a heart dissimilarly to other types of signals. For example, the authentication apparatus uses a relatively small number of internal nodes including sub-neural networks corresponding to the P wave, the QRS wave, and the T wave, each representing a different characteristic of the ECG signal, thereby enhancing an accuracy of an authentication.

The method performs a max pooling on a plurality of feature values corresponding to the hidden layer node 230 in operation 240. For example, the authentication apparatus performs a max pooling on a plurality of feature values corresponding to the hidden layer node 230 in operation 240. As an example, the authentication apparatus extracts an upper value in a preset range as the feature value. As another example, the authentication apparatus extracts a first feature value corresponding to a highest value from among the plurality of feature values as a feature value corresponding to an input ECG signal. Based on a time shifting feature of the ECG signal, the authentication apparatus is implemented such that the identical weight set is shared in the hidden layer node 230. Thus, the first hidden node 231 to the seventh hidden node 237 having a highest feature value output a feature value associated with a sampling interval during which the ECG signal is actually input. Accordingly, the authentication apparatus determines an output value by performing the max pooling on an output value of the hidden layer node 230 in operation 240 and thus, stably outputs the feature value corresponding to the input ECG signal despite a time shifting.

Therefore, FIG. 2C illustrates a process of extracting four feature values corresponding to the input ECG signal in an output layer node 250 as an example. Accordingly, the number of feature values varying based on a machine learning of the neural network is to be output as the feature value corresponding to the input ECG signal.

Figure 2D:
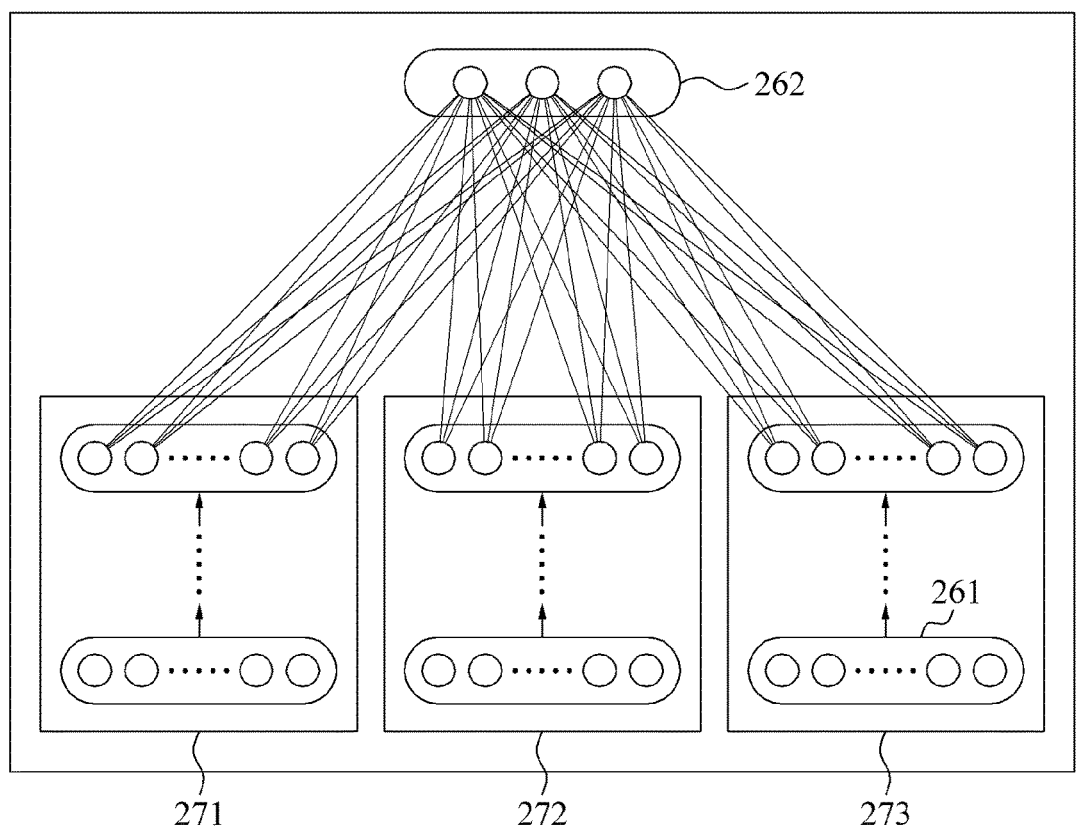
FIG. 2D is a diagram illustrating an example of extracting a feature value based on a neural network in accordance with an embodiment.

FIG. 2D is a diagram illustrating an example of extracting a feature value based on a neural network in accordance with an embodiment.

FIG. 2D illustrates a neural network 260 included in an authentication apparatus. In the example of FIG. 2D, the neural network 260 includes an input layer node 261 that receives an input ECG signal and an output layer node 262 that outputs a feature value corresponding to the input ECG signal. In such an example, the neural network 260 includes three sub-neural networks. For example, the neural network 260 includes a first sub-neural network 271, a second sub-neural network 272, and a third sub-neural network 273. In this example, the first sub-neural network 271 extracts a feature value of a P wave from the input ECG signal. The second sub-neural network 272 extracts a feature value of a QRS wave from the input ECG signal. The third sub-neural network 273 extracts a feature value of a T wave from the input ECG signal. Accordingly, the neural network and sub-neural network operate so as to provide specialized analysis of various waveforms of the input ECG signal. Also, the feature value of the input ECG signal is calculated by fully connecting and combining the feature values of the first sub-neural network 271, the second sub-neural network 272, and the third sub-neural network 273. A number of nodes included in each of the three sub-neural networks and weights to be assigned to the nodes are determined accordingly based on a result of machine learning. The machine learning performed by the authentication apparatus to perform an authentication is described further with reference to the drawing below.

Figure 3:
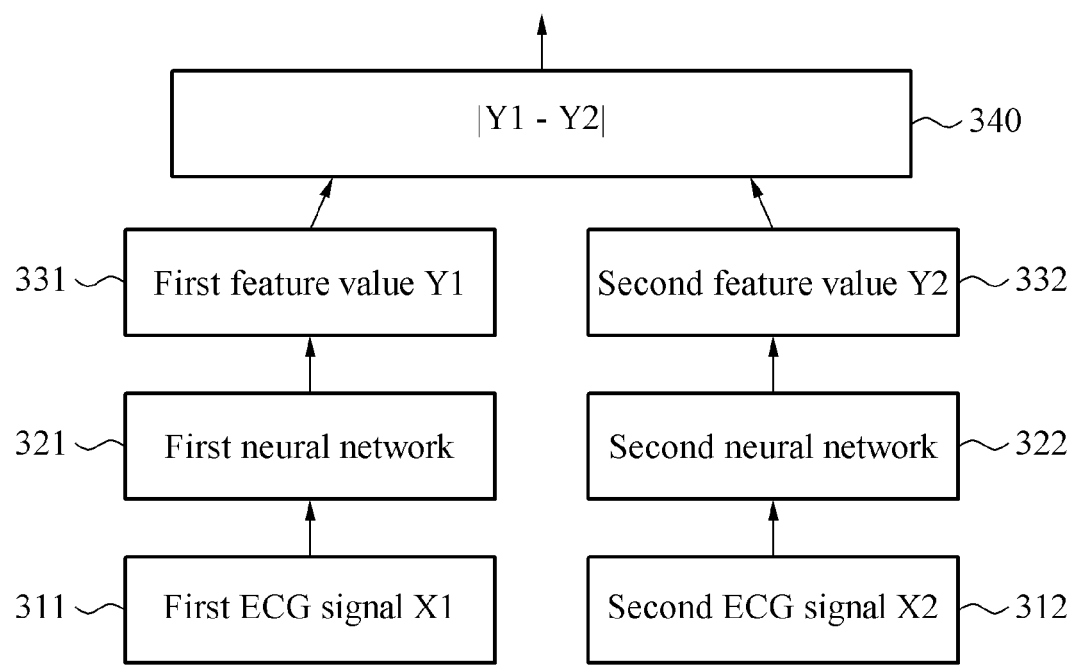
FIG. 3 is a diagram illustrating an example of a machine learning of a neural network in accordance with an embodiment.

FIG. 3 is a diagram illustrating an example of a machine learning of a neural network in accordance with an embodiment.

FIG. 3 illustrates a process of machine learning that is performed by an authentication apparatus in order to extract a feature value. In the example of FIG. 3, the authentication apparatus extracts a feature value for authenticating a user by using a Siamese neural network, for example, a first neural network 321 and a second neural network 322. Here, the Siamese neural network refers to identical, complementary neural networks. For example, the first neural network 321 and the second neural network 322 share attributes such as the number of nodes, the weight, and a connection relationship.

In the example of FIG. 3, a first ECG signal X1 311 is input to the first neural network 321. Likewise, in the example of FIG. 3, a second ECG signal X2 312 is input to the second neural network 322. A first feature value Y1 331 and a second feature value Y2 322 corresponding to the first ECG signal X1 311 and the second ECG signal X2 312 input to the first neural network 321 and the second neural network 322 are calculated as output values by using the neural networks. Also, the authentication apparatus previously stores identification information of a user associated with the first ECG signal X1 311 and the second ECG signal X2 312. Based on such identification information, the authentication apparatus performs the machine learning such that a difference value |Y1−Y2| 340 between feature values 331 and 332 is found to be relatively small when ECG signals are acquired from the same user. Also, the authentication apparatus performs the machine learning such that the difference value |Y1−Y2| 340 between the feature values 331 and 332 is found to be relatively large when ECG signals are acquired from different users. These similarities and differences are derived in this manner because the machine learning adapts the neural network to provide results in this manner. Accordingly, based on a result of the machine learning, a feature value for quickly and accurately determining an ECG signal corresponding to each registered user is verified.

Figure 4A:
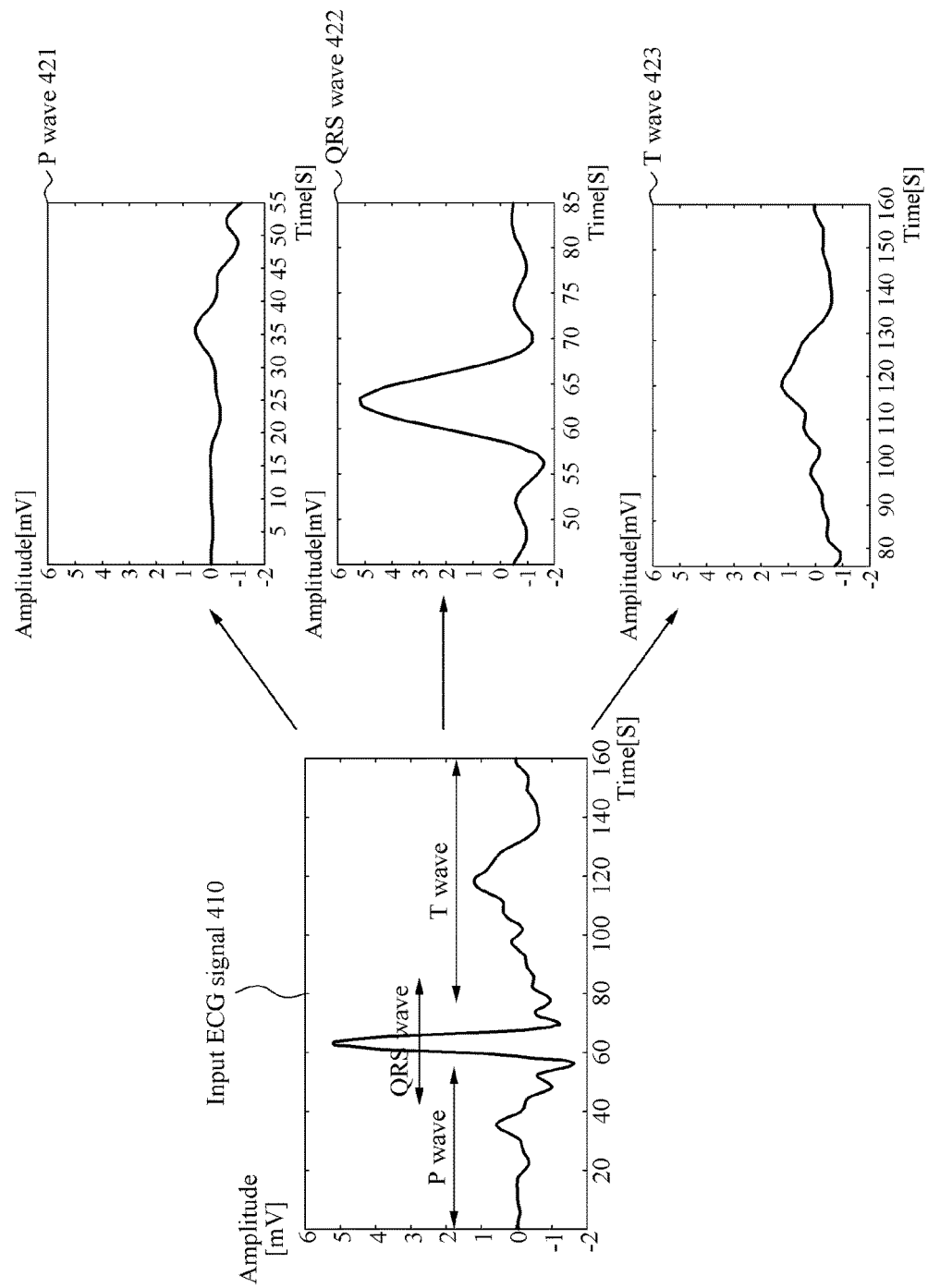

FIGS. 4A and 4B are diagrams illustrating an example of generating a sub-neural network for each interval signal of an ECG signal in accordance with an embodiment.

FIG. 4A illustrates a graph of a P wave 421, a QRS wave 422, a T wave 423, and an input ECG signal 410 that are acquired from a biosignal input to an authentication apparatus. In the graph, an X axis represents a time in seconds and a Y axis represents an amplitude having a unit of mV. The authentication apparatus extracts the P wave 421, the QRS wave 422, and the T wave 423 from the input ECG signal 410 corresponding to one period of the ECG signal 410. For example, the authentication apparatus extracts the QRS wave 422 using an average value of QRS intervals based on a position of an R peak and extracts interval signals separated by the QRS wave 422 as the P wave 421 and the T wave 423. However, the present disclosure is not limited to such an example. Thus, the authentication apparatus extracts each of the P wave 421, the QRS wave 422, and the T wave 423 in different ways based on various extraction methods.

FIG. 4B illustrates a first sub-neural network 431 corresponding to the P wave 421, a second sub-neural network 432 corresponding to the QRS wave 422, and a third sub-neural network 433 corresponding to the T wave 423. In the example of FIG. 4B, the authentication apparatus inputs the P wave 421, the QRS wave 422, and the T wave 423 previously extracted from the input ECG signal 410 to input nodes of each of the first sub-neural network 431, the second sub-neural network 432, and the third sub-neural network 433. For example, the inputs of the P wave 421, the QRS wave 422, and the T wave 423 were previously extracted from the input ECG signal 410 as per FIG. 4A. Each of the first sub-neural network 431, the second sub-neural network 432, and the third sub-neural network 433 calculates an output value of a corresponding hidden layer node by applying a different weight to the P wave 421, the QRS wave 422, and the T wave 423. Hence, the machine learning facilitates processing these parts of the input ECG signal 410 in a facilitated manner with better performance. In this example, the example of FIGS. 2A and 2B illustrating that the identical weight set is applied to each of the input node sets is also applicable for understanding the example.

For example, the authentication apparatus generates the first sub-neural network 431, the second sub-neural network 432, and the third sub-neural network 433 corresponding to the P wave 421, the QRS wave 422, and the T wave 423, respectively. The authentication apparatus generates the first sub-neural network 431, the second sub-neural network 432, and the third sub-neural network 433 as being independent of one another through a machine learning, such as based on a prestored reference ECG signal. The reference ECG signal includes, for example, an ECG signal corresponding to an unidentified user as well as an ECG signal corresponding to a registered user. In such an example, the unidentified user may be a user differing from the registered user.

Based on the machine learning, the authentication apparatus determines a connection relationship of nodes, a number of hidden layer nodes, a size of a weight for an input node set, and a number of input layer nodes for each of the first sub-neural network 431, the second sub-neural network 432, and the third sub-neural network 433. In this example, each of the first sub-neural network 431, the second sub-neural network 432, and the third sub-neural network 433 has a simple connection relationship of nodes when compared to a neural network for processing the input ECG signal 410 overall. Also, in such an example, the number of hidden layer nodes connecting an input layer node and an output layer node in a neural network may decrease. The authentication apparatus generates the first sub-neural network 431, the second sub-neural network 432, and the third sub-neural network 433 as independently corresponding to each of the P wave 421, the QRS wave 422, and the T wave 423, thereby avoiding an overfitting output value which may be calculated based on the prestored reference ECG signal, which possibly occurs in other approaches.

Figure 5:
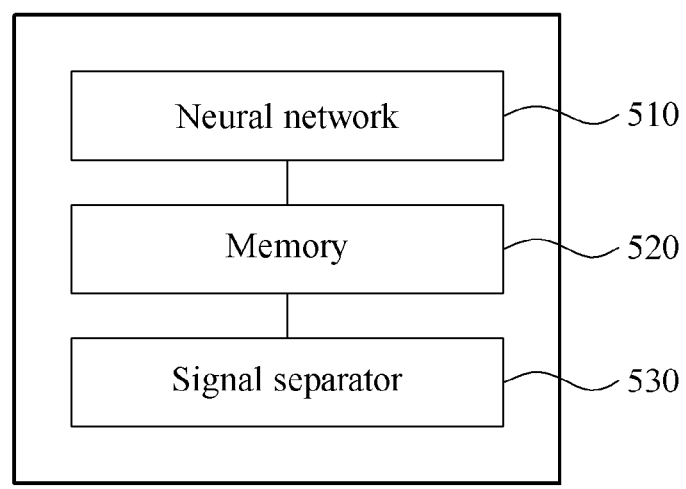
FIG. 5 is a block diagram illustrating an example of an authentication apparatus in accordance with an embodiment.

FIG. 5 is a block diagram illustrating an example of an authentication apparatus in accordance with an embodiment.

Referring to the embodiment of FIG. 5, an authentication apparatus 500 includes a neural network 510, a memory 520, and a signal separator 530. For example, the authentication apparatus 500 performs a machine learning to authenticate a user based on a prestored reference ECG signal. For example, based on the machine learning, the neural network 510 groups a preset number of input nodes into an input node set and calculates an output value by applying an identical weight set assigned to the input node set. However, it is to be noted that the authentication apparatus 500 is not to be limited to these elements alone, and in other embodiments the authentication apparatus 500 may include additional elements, as appropriate.

The authentication apparatus 500 is implemented as, for example, a portable electronic device. The portable electronic device may be implemented as, for example a laptop computer, a mobile phone, a smart phone, a tablet PC, a mobile internet device (MID), a personal digital assistant (PDA), an enterprise digital assistant (EDA), a digital still camera, a digital video camera, a portable multimedia player (PMP), a personal navigation device or portable navigation device (PND), a handheld consol, an e-book, and a smart device. The smart device may be implemented to be, for example, a smart watch and a smart band. However, these are merely examples of possible candidate devices that are portable electronic devices or smart devices, and other examples include alternative types of devices, as appropriate.

The neural network 510 groups an input node included in the neural network 510 into an input node set to which an identical weight set is assigned. In an example, the neural network 510 groups input nodes receiving an ECG signal within a predetermined time range into the input node set. Also, the neural network 510 generates a hidden layer node corresponding to the input node set. Furthermore, the neural network 510 matches the hidden layer node and the output value, appropriately.

In another example, the neural network 510 connects a plurality of hidden nodes to input node sets that include a preset number of input nodes, determined based on the machine learning. Thus, the hidden nodes of the plurality of hidden nodes share the identical weight set and are connected to the input node sets, respectively.

Also, the neural network 510 extracts a feature value corresponding to the hidden layer node by applying a weight to an ECG signal input to each input node. For example, one input node set matches one hidden layer node. In this manner, the neural network 510 sequentially connects the plurality of hidden nodes to the input node sets.

In the embodiment of FIG. 5, the memory 520 registers a feature value calculated using an input ECG signal associated with a user and the neural network 510 by matching the feature value and the user, as discussed further, above. Also, the memory 520 stores a plurality of reference ECG signals of users differing from a registered user. These reference ECG signals of users differing from a registered user help disambiguate signals by clarifying when signals are the same and when they are different.

In the embodiment of FIG. 5, the signal separator 530 separates at least one interval signal of a P wave, a QRS wave, and a T wave from the input ECG signal. For example, the signal separator 530 extracts a position of an R peak from the input ECG signal. Also, the signal separator 530 extracts, as the QRS wave, an upward wave including the R peak, a downward wave extracted after the upward wave, and a downward wave recorded before the upward wave. These operations are described as an example. However, in other examples, the signal separator 530 also separates at least one interval signal of the P wave, the QRS wave, and the T wave from the input ECG signal based on various signal separation methods. As discussed above, various analytical techniques help facilitate such signal separation methods.

For example, the neural network 510 includes a sub-neural network corresponding to at least one interval signal. In an example, the neural network 510 includes three independent neural networks having a connection relationship, a size of a parameter, and the number of nodes corresponding to each of the P wave, the QRS wave, and the T wave.

In the embodiment of FIG. 5, the neural network 510 sets an initial setting value of the neural network 510 based on the prestored reference ECG signal. For example, the neural network 510 sets at least one of a size of the weight applied to the input node set, the number of input nodes included in the input node set, and a distance between the input nodes to be the initial setting value. Also, the neural network 510 adjusts the initial setting value based on a registered ECG signal that corresponds to the registered user. The neural network 510 additionally performs the machine learning based on the registered ECG signal after the machine learning is performed based on the reference ECG signal. In the embodiment of FIG. 5, the authentication apparatus 500 performs a fine tuning operation based on the registered ECG signal corresponding to the registered user, thereby quickly and accurately authenticating the registered user.

Figure 6:
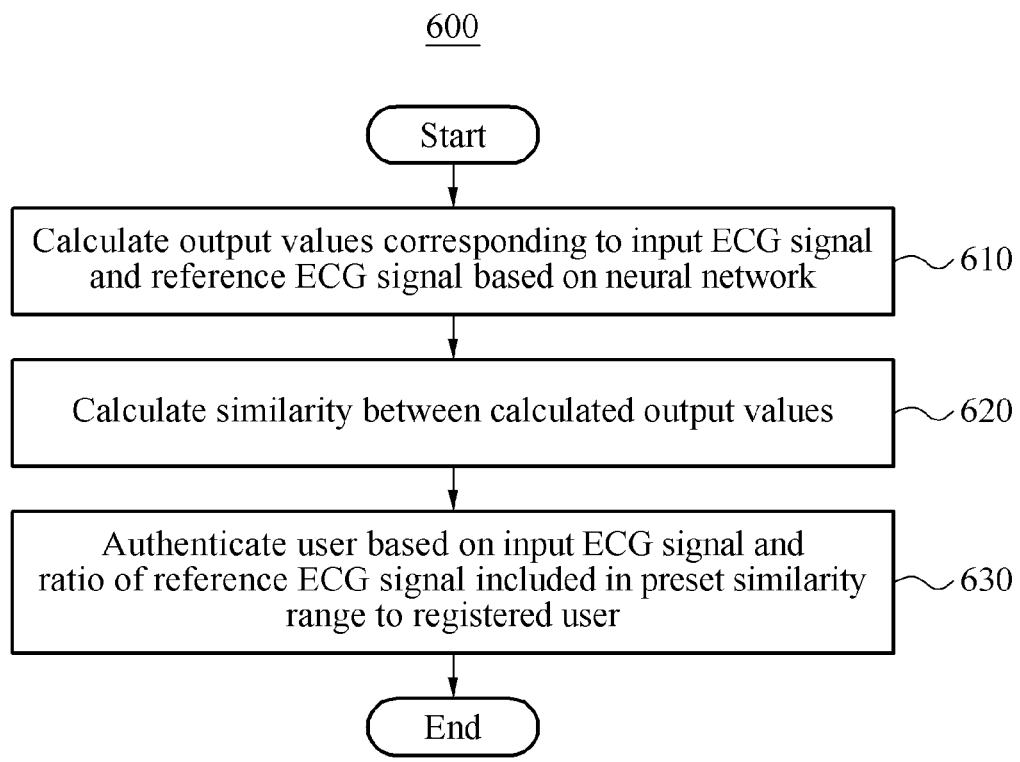
FIG. 6 is a flowchart illustrating an example of an operation of an authentication apparatus in accordance with an embodiment.

FIG. 6 is a flowchart illustrating an example of an operation of an authentication apparatus in accordance with an embodiment. For example, the operations of FIG. 6 may be performed by an authentication apparatus.

Referring to the embodiment of FIG. 6, in operation 610, a method calculates output values corresponding to an input ECG signal and a reference ECG signal based on a neural network. The output values each indicate a feature value matching a registered ECG signal and that are stored in a memory of the authentication apparatus in advance. In an example, the method calculates the output values based on a first neural network corresponding to the input ECG signal and a second neural network corresponding to the reference ECG signal. The first neural network and the second neural network are, for example, Siamese neural networks sharing weights assigned to internal nodes with each other. The Siamese neural networks used in a process of user authentication are described further in detail with reference to the drawing below. In this example, the input ECG signal is an ECG signal of a user that is in contact with the authentication apparatus. Also, for example, the reference ECG signal is an ECG signal previously stored in the authentication apparatus. In an example, the reference ECG signal is associated with one of a registered user and an unidentified user corresponding to a user differing from the registered user. Depending on an example, the authentication apparatus has one registered user or alternatively has a plurality of registered users.

In operation 610, the authentication apparatus acquires a plurality of input ECG signals of a target user on which a user authentication is to be performed based on an ECG signal, and extracts a P wave, a QRS wave, and a T wave from each of the plurality of input ECG signals. Since the descriptions related to operations 110 and 120 of FIG. 1 are also applicable here, repeated descriptions will be omitted for brevity.

In operation 620, the method calculates a similarity between the calculated output values. For example, the method calculates the similarity between the output values by comparing output values corresponding to the input ECG signal and the reference ECG signal. Such similarity may be calculated by using, for example, a norm, a root-mean-square (RMSE), a correlation, and a cosine similarity. However, these are only example metrics, and other methods of assessing similarity are used in other examples.

In operation 630, the method authenticates a user based on the input ECG signal and a ratio of a reference ECG signal that is included in a preset similarity range to a registered user. For example, the method extracts the input ECG signal and the reference ECG signal included in the preset similarity range based on a k-nearest neighborhood algorithm. However, this is only a sample of an algorithm that may be used to extract the input ECG signal and the reference ECG signal and other appropriate algorithms may also be used.

In an example, the method calculates a ratio of the reference ECG signal to a registered ECG signal that is associated with the registered user. When the calculated ratio is a highest ratio from among ratios of other users, a user in contact with the authentication apparatus is authenticated to be the registered user. That is, the method considers all of the possible identities of previously registered users, determines which is most likely to be the registered user, and determines such a user to be the registered user.

In another example, when the ratio of the reference ECG signal to the registered ECG signal associated with the registered user is higher than or equal to a threshold, the method authenticates the user in contact with the authentication apparatus to be the registered user. Thus, in such approach, the method establishes that it is sufficiently likely that the user is the correctly authenticated user. The k-nearest neighborhood algorithm used in the authentication apparatus is described in further detail with reference to the drawing below.

Figure 7:
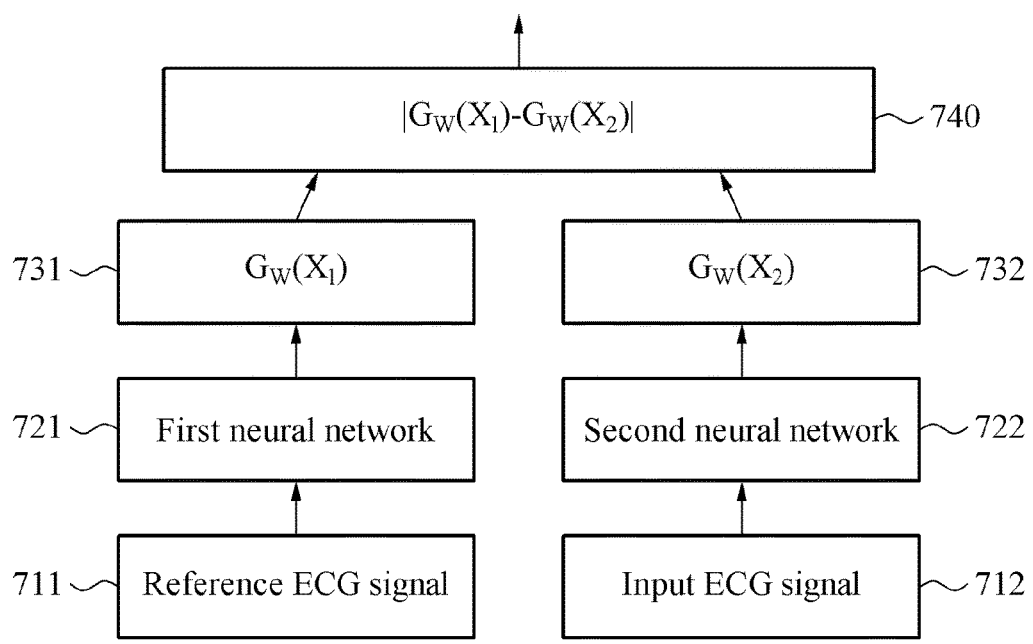
FIG. 7 is a diagram illustrating an example of an operation of a Siamese neural network in accordance with an embodiment.

FIG. 7 is a diagram illustrating an example of an operation of a Siamese neural network in accordance with an embodiment.

Referring to the embodiment of FIG. 7, an authentication apparatus inputs a prestored reference ECG signal 711 and an input ECG signal 712 acquired from a user into a Siamese neural network. For example, the reference ECG signal 711 is input to a first neural network 721 and the input ECG signal 712 is input to a second neural network 722. In such an example, the first neural network 721 and the second neural network 722 included in the Siamese neural network are neural networks sharing at least one of a connection relationship of nodes, the number of internal nodes, a size of weight, and a size of a parameter.

The first neural network 721 calculates $G_w(X_1)$ 731 as an output value of the first neural network 721. Similarly, the second neural network 722 calculates $G_w(X_2)$ 732 as an output value of the second neural network 722. In this example, the authentication apparatus stores a plurality of ECG signals as the reference ECG signal. The reference ECG signal is an ECG signal associated with a registered user, and is also an ECG signal associated with a user differing from the registered user. Hence, the reference ECG signal includes information about the registered user as well as other users. Thus, the first neural network 721 calculates a plurality of values of $G_w(X_1)$ 731 as the output value 731 of the first neural network 721. The first neural network 721 and the second neural network 722 are included in the Siamese neural network and thus, calculate output values of which similarities increases according to an increase in similarities of input data. Accordingly, the output values are appropriate values for assessing whether the reference ECG signal 711 and the input ECG signal 712 are related. For example, when the reference ECG signal 711 is similar to the input ECG signal 712, a similarity 740 between $G_w(X_1)$ 731 and $G_w(X_2)$ 732 is relatively high, such that the absolute value of the difference between $G_w(X_1)$ 731 and $G_w(X_2)$ 732 is small. Also, when the reference ECG signal 711 is different from the input ECG signal 712, the similarity 740 between $G_w(X_1)$ 731 and $G_w(X_2)$ 732 is relatively low, and the difference between these values is relatively great.

In an example, the authentication apparatus applies a k-nearest neighborhood algorithm to one value of $G_w(X_2)$ 732 corresponding to the input ECG signal 712 and a plurality of values of $G_w(X_1)$ 731 corresponding to a plurality of reference ECG signals including the reference ECG signal 711. Accordingly, the authentication apparatus determines whether a user associated with the input ECG signal 712 is the registered user, based on the results of the k-nearest neighborhood algorithm. The foregoing example is described in further detail with reference to the drawing below.

Figure 8:
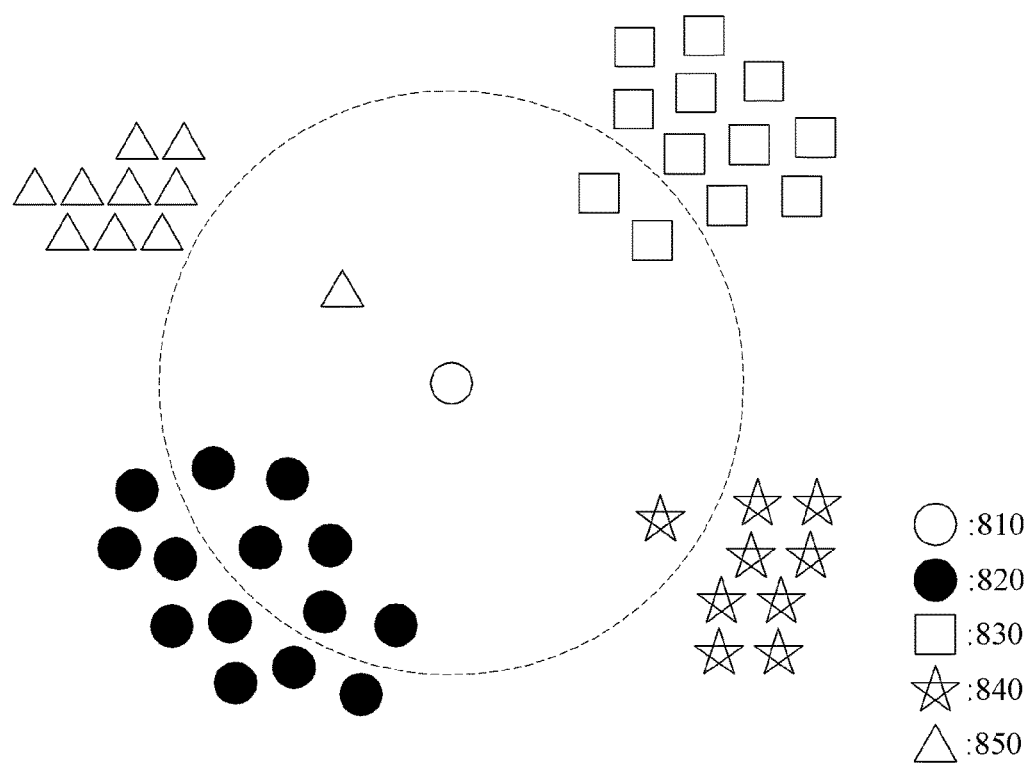
FIG. 8 is a diagram illustrating an example of an authentication apparatus applying a k-nearest neighborhood algorithm in accordance with an embodiment.

FIG. 8 is a diagram illustrating an example of an authentication apparatus applying a k-nearest neighborhood algorithm in accordance with an embodiment.

FIG. 8 illustrates a plurality of output values acquired from each of an input ECG signal and a reference ECG signal. For example, an authentication apparatus acquires a first output value 810 based on an input ECG signal of a user. The user is, for example, a user that is in contact with the authentication apparatus, such that the user is to be authenticated. The authentication apparatus acquires a plurality of second output values including, for example, an output value 820 and output values 830, 840, and 850 based on a prestored reference ECG signal. These output values are illustrated using appropriate symbols in the example of FIG. 8. As presented in the foregoing, the reference ECG signal includes an ECG signal associated with a user that is registered in the authentication apparatus and an ECG signal associated with an unidentified user differing from the registered user. Thus, the authentication apparatus acquires a plurality of output values 820 based on the ECG signal associated with the registered user. Also, the authentication apparatus acquires a plurality of output values 830, 840, or 850 based on the ECG signal associated with the unidentified user. As a result, these output values may be considered for use in the example of FIG. 8. The ECG signal associated with the unidentified user includes, for example, ECG signals associated with a plurality of users differing from one another.

The authentication apparatus extracts second output values in a preset similarity range based on the first output value 810. In an example, the authentication apparatus extracts a preset number of second output values in an ascending order of similarities with the first output value 810. For example, the example of FIG. 8 illustrates that 10 different second output values are extracted as an example (i.e., the 6 output values 820, 2 output values 830, 1 output value 940, and 1 output value 850 inside the dashed circle) and thus, the number of extracted second output values is not to be limited to such an example.

Additionally, the authentication apparatus calculates a ratio of the number of the extracted second output values 820 associated with the registered user (6 in FIG. 8) to the total number of extracted second output values (10 in FIG. 8). When the calculated ratio is higher than ratios of the numbers of the other extracted second output values 830, 840, and 850 associated with other users (2, 1, and 1 in FIG. 8) to the total number of the extracted second output values, the authentication apparatus authenticates the user in contact with the authentication apparatus to be the registered user. For example, the ratio of the number of the extracted second output values 820 is calculated to be 60% (6/10). The ratios of the numbers of the other extracted second output values 830, 840, and 850 to the total number of the extracted output values are each calculated to be 20% or 10% (2/10 or 1/10). Thus, the authentication apparatus authenticates the user in contact with the authentication apparatus to be the registered user.

In another example, when a ratio of the output values 820 associated with the registered user to the extracted second output values is higher than or equal to a threshold, the authentication apparatus authenticates the user in contact with the authentication apparatus to the registered user. In this example, the threshold is, for example, a value that is adjusted based on a security consideration for the authentication apparatus. The authentication apparatus is potentially implemented in various forms. For example, the authentication apparatus is a PC, a laptop computer, a tablet computer, a smartphone, a smart appliance, a television, an intelligence vehicle, and a wearable device. However, these are only examples of an authentication apparatus, and other electronic devices are used as the authentication apparatus in other examples. To be applied in, for example, a payment service based on a high security authentication, the threshold is adjusted to have a relatively high value. Without having a relatively high threshold, it cannot be reliably guaranteed that the authentication apparatus only authenticates users that are actually legitimate users.

In the example of FIG. 8, a proportion of the output values 820 included in the ten extracted second output values is 60%. When the threshold is set to, for example, 50%, the authentication apparatus authenticates the user in contact with the authentication apparatus to be the registered user, because there is sufficient evidence to determine that authentication should occur.

Figure 9:
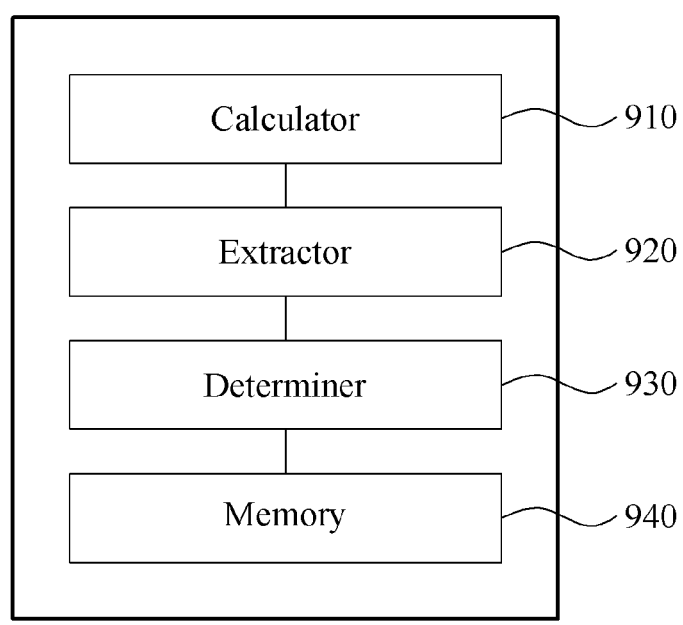
FIG. 9 is a block diagram illustrating another example of an authentication apparatus in accordance with an embodiment.

FIG. 9 is a block diagram illustrating another example of an authentication apparatus in accordance with an embodiment.

Referring to the embodiment of FIG. 9, an authentication apparatus 900 includes a calculator 910, an extractor 920, a determiner 930, and a memory 940. In the example of FIG. 9, the calculator 910 calculates a first output value corresponding to an input ECG signal based on a neural network. Aspects of such calculation are discussed further, above. Also, the calculator 910 calculates a plurality of second output values, each corresponding to a reference ECG signal based on the neural network. For example, the reference ECG signal is an ECG signal associated with one of an unidentified user and a registered user. The calculator 910 calculates the first output value and the plurality of second output values by applying a weight of the neural network determined through a machine learning process, as discussed further, above. For example, the calculator 910 calculates the first output value and the plurality of second output values by calculating a sum of weights assigned to nodes in the neural network.

The extractor 920 extracts a preset number of second output values from the plurality of second output values based on the first output value. In an example, the extractor 920 extracts the preset number of second output values in an ascending order of differences from the first output value. The determiner 930 determines whether to authenticate a user based on a ratio of the reference ECG signal corresponding to each of the extracted second output values to corresponding values for the registered user. The determiner 930 authenticates a user associated with the input ECG signal to be the registered user when a ratio of the reference ECG signal corresponding to each of the extracted second output values to the values associated with the registered user is higher or equal to a threshold. When the ratio is lower than a threshold, the determiner 930 outputs an authentication failure message or a re-authentication request message to the user, because such a result indicates that the ECG signal cannot be determined to be sufficiently similar to characteristics of a registered user's ECG characteristics to confirm authentication.

In another example, the extractor 920 repetitively extracts second output values in the ascending order of differences from the first output value. In this example, the number of the extracted second output values varies for each extraction. For example, the extractor 920 repetitively extracts $k_1$ second output values, $k_2$ second output values, and $k_3$ second output values in the ascending order of differences from the first output value. In such an example, the determiner 930 calculates a first ratio of a reference ECG signal corresponding to each of the $k_1$ second output values to the corresponding values for the registered user. Similarly, the determiner 930 calculates a second ratio of a reference ECG signal corresponding to each of the $k_2$ second output values to the corresponding values for the registered user. Also, the determiner 930 calculates a third ratio of a reference ECG signal corresponding to each of the $k_3$ second output values to the corresponding values for the registered user. The determiner 930 compares each of the first ratio, the second ratio, and the third ratio to a threshold. When the number of cases in which the ratios are calculated to be higher than or equal to a threshold is larger than the number of cases in which the ratios are calculated to be lower than the threshold, the determiner 930 authenticates the user associated with the input ECG signal to be the registered user, as the comparison is indicative of sufficient similarity.

The memory 940 stores a reference ECG signal used for a user authentication. For example, the memory 940 stores a plurality of ECG signals corresponding to a plurality of different points in time of the registered user as the reference ECG signal. These reference values are used for comparison when authenticating, as discussed above. The authentication apparatus 900 previously stores reference ECG signals corresponding to various body states of the registered user to avoid an overfitting result of machine learning. For example, as discussed above, the same user may have different ECG signals depending on, for example, whether the user has recently ingested caffeine. When a user in contact with the authentication apparatus 900 is authenticated as the registered user as discussed, the determiner 930 stores the input ECG signal in the memory 940 as a reference ECG signal associated with the registered user, for use in subsequent authentications.

The apparatuses, units, modules, devices, and other components illustrated in FIGS. 1-9 that perform the operations described herein with respect to FIGS. 1-9 are implemented by hardware components. Examples of hardware components include controllers, sensors, generators, drivers, memories, comparators, arithmetic logic units, adders, subtractors, multipliers, dividers, integrators, neural networks, signal separators, calculators, extractors, determiners, and any other electronic components known to one of ordinary skill in the art. In one example, the hardware components are implemented by computing hardware, for example, by one or more processors or computers. A processor or computer is implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices known to one of ordinary skill in the art that is capable of responding to and executing instructions in a defined manner to achieve a desired result. In one example, a processor or computer includes, or is connected to, one or more memories storing instructions or software that are executed by the processor or computer. Hardware components implemented by a processor or computer execute instructions or software, such as an operating system (OS) and one or more software applications that run on the OS, to perform the operations described herein with respect to FIGS. 1-9. The hardware components also access, manipulate, process, create, and store data in response to execution of the instructions or software. For simplicity, the singular term "processor" or "computer" may be used in the description of the examples described herein, but in other examples multiple processors or computers are used, or a processor or computer includes multiple processing elements, or multiple types of processing elements, or both. In one example, a hardware component includes multiple processors, and in another example, a hardware component includes a processor and a controller. A hardware component has any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-9 that perform the operations described herein with respect to FIGS. 1-9 are performed by computing hardware, for example, by one or more processors or computers, as described above executing instructions or software to perform the operations described herein.

Instructions or software to control a processor or computer to implement the hardware components and perform the methods as described above are written as computer programs, code segments, instructions or any combination thereof, for individually or collectively instructing or configuring the processor or computer to operate as a machine or special-purpose computer to perform the operations performed by the hardware components and the methods as described above. In one example, the instructions or software include machine code that is directly executed by the processor or computer, such as machine code produced by a compiler. In another example, the instructions or software include higher-level code that is executed by the processor or computer using an interpreter. Programmers of ordinary skill in the art can readily write the instructions or software based on the block diagrams and the flow charts illustrated in the drawings and the corresponding descriptions in the specification, which disclose algorithms for performing the operations performed by the hardware components and the methods as described above.

The instructions or software to control a processor or computer to implement the hardware components and perform the methods as described above, and any associated data, data files, and data structures, are recorded, stored, or fixed in or on one or more non-transitory computer-readable storage media. Examples of a non-transitory computer-readable storage medium include read-only memory (ROM), random-access memory (RAM), flash memory, CD-ROMs, CD-Rs, CD+Rs, CD-RWs, CD+RWs, DVD-ROMs, DVD-Rs, DVD+Rs, DVD-RWs, DVD+RWs, DVD-RAMs, BD-ROMs, BD-Rs, BD-R LTHs, BD-REs, magnetic tapes, floppy disks, magneto-optical data storage devices, optical data storage devices, hard disks, solid-state disks, and any device known to one of ordinary skill in the art that is capable of storing the instructions or software and any associated data, data files, and data structures in a non-transitory manner and providing the instructions or software and any associated data, data files, and data structures to a processor or computer so that the processor or computer can execute the instructions. In one example, the instructions or software and any associated data, data files, and data structures are distributed over network-coupled computer systems so that the instructions and software and any associated data, data files, and data structures are stored, accessed, and executed in a distributed fashion by the processor or computer.

While this disclosure includes specific examples, it will be apparent to one of ordinary skill in the art that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents. Therefore, the scope of the disclosure is defined not by the detailed description, but by the claims and their equivalents, and all variations within the scope of the claims and their equivalents are to be construed as being included in the disclosure.

What is claimed is:

1. An authentication apparatus comprising:
one or more processors configured to
implement a neural network comprising an input layer comprising N input nodes and a hidden layer comprising hidden nodes, wherein the hidden layer is connected to the input layer;
group the input nodes into input node sets comprising M input nodes, wherein M is less than N,
wherein each input node set is connected to a single respective hidden node, and
wherein each hidden node of the hidden nodes is connected to a single respective input node set;
assign a first weight set comprising weights to each input node set of the input node sets;

calculate a respective feature value for each hidden node based on the respective input node set connected to the each hidden node and the first weight set;

determine at least one output feature value based on the respective feature value for each hidden node; and register a user in association with an input electrocardiogram (ECG) signal and the at least one output feature value, wherein the first weight set is the same weight set applied to every input node set of the input node sets.

2. The authentication apparatus of claim 1, wherein the one or more processors are further configured to group the input nodes into the input nodes sets by:

forming a first input node set comprising input nodes 1 to M;

forming a second input node set comprising input nodes 2 to M+1; and forming successive input nodes sets by successively subtracting a first input node in a previous input node set and adding a new input node to the remaining input nodes of the previous input node set until all N input nodes have been assigned to an input node set, such that each successive input node set differs from an input node set created before and an input node set created after the each successive input node set by one node.

3. The authentication apparatus of claim 1, wherein the one or more processors are further configured to:

separate an interval signal of a P wave, a QRS wave, and a T wave from the ECG signal;

determine respective weight sets based on the interval signals; and calculate the at least one output feature value based on the determined respective weight sets.

4. The authentication apparatus of claim 3, wherein:

the neural network comprises at least one of a first sub-neural network having a P-wave weight set corresponding to the P wave, a second sub-neural network having a QRS-wave weight set corresponding to the QRS wave, or a third sub-neural network having a T-wave weight set corresponding to the T wave; and the first weight set comprises the P-wave weight set, the QRS-wave weight set, and the T-wave weight set.

5. The authentication apparatus of claim 1, wherein the one or more processors are further configured to:

divide the ECG signal into a number of time periods of an equal length of time; and set a number of input nodes in the input layer to be equal to the number of time periods of the ECG signal, wherein each time period corresponds to a single respective input node.

6. The authentication apparatus of claim 1, wherein the one or more processors are further configured to group the input nodes into the input node sets by assigning input nodes that receive the ECG signal within a predetermined time range into a same input node set.

7. The authentication apparatus of claim 1, wherein the one or more processors are further configured to determine the at least one output feature value by extracting an upper value in a range from among the respective feature values of the hidden nodes as the at least one output feature value.

8. The authentication apparatus of claim 1, wherein a number of input nodes in each input node set is determined based on machine learning.

* * * * *